(12) United States Patent
Hermann et al.

(10) Patent No.: US 6,305,908 B1
(45) Date of Patent: *Oct. 23, 2001

(54) INFUSION PUMP EXTRUDED METAL HOUSING WITH ELASTOMERIC END CAPS

(75) Inventors: Robert A. Hermann, Chula Vista; Michael W. Lawless, Poway; Peter A. Soberon, San Diego, all of CA (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/100,047

(22) Filed: Jun. 19, 1998

(51) Int. Cl.[7] ...................................................... F04B 53/00
(52) U.S. Cl. .............................................................. 417/234
(58) Field of Search ..................................... 417/234, 231, 417/232, 233; 604/4, 6, 7, 131, 65

(56) References Cited

U.S. PATENT DOCUMENTS

| 4,741,736 | 5/1988 | Brown . |
| 4,890,984 | 1/1990 | Alderson et al. . |
| 5,370,622 | 12/1994 | Livingston et al. . |
| 5,415,038 | 5/1995 | Rynhart et al. . |
| 5,472,317 | 12/1995 | Field et al. . |
| 5,482,446 | 1/1996 | Williamson et al. . |
| 5,540,561 | 7/1996 | Johnson . |
| 5,718,562 | 2/1998 | Lawless et al. . |

FOREIGN PATENT DOCUMENTS

98/04316   2/1998   (WO) .

Primary Examiner—Teresa Walberg
Assistant Examiner—Daniel Robinson
(74) Attorney, Agent, or Firm—Beth A. Vrioni

(57) ABSTRACT

A housing for a medicinal pump, which is sealed to prevent damage due to exposure of the housing to water or other liquids. The housing includes an extruded case in which the various components comprising the pump are enclosed. The ends of the extruded case are sealed by a top cap and a bottom cap that are overmolded with an elastomeric material. The elastomeric material seals the top and bottom caps against the extruded case and provides shock resistance to protect the pump from damage. An open side of the pump is sealed with a pump chassis that supports a pump cassette used to infuse medicinal fluids into a patient. A bezel assembly on the front surface of the pump is adhesively attached thereto using a double-sided adhesive sheet. The double sided adhesive sheet seals the openings for a display and a keypad formed in the front surface of the extruded case.

27 Claims, 5 Drawing Sheets

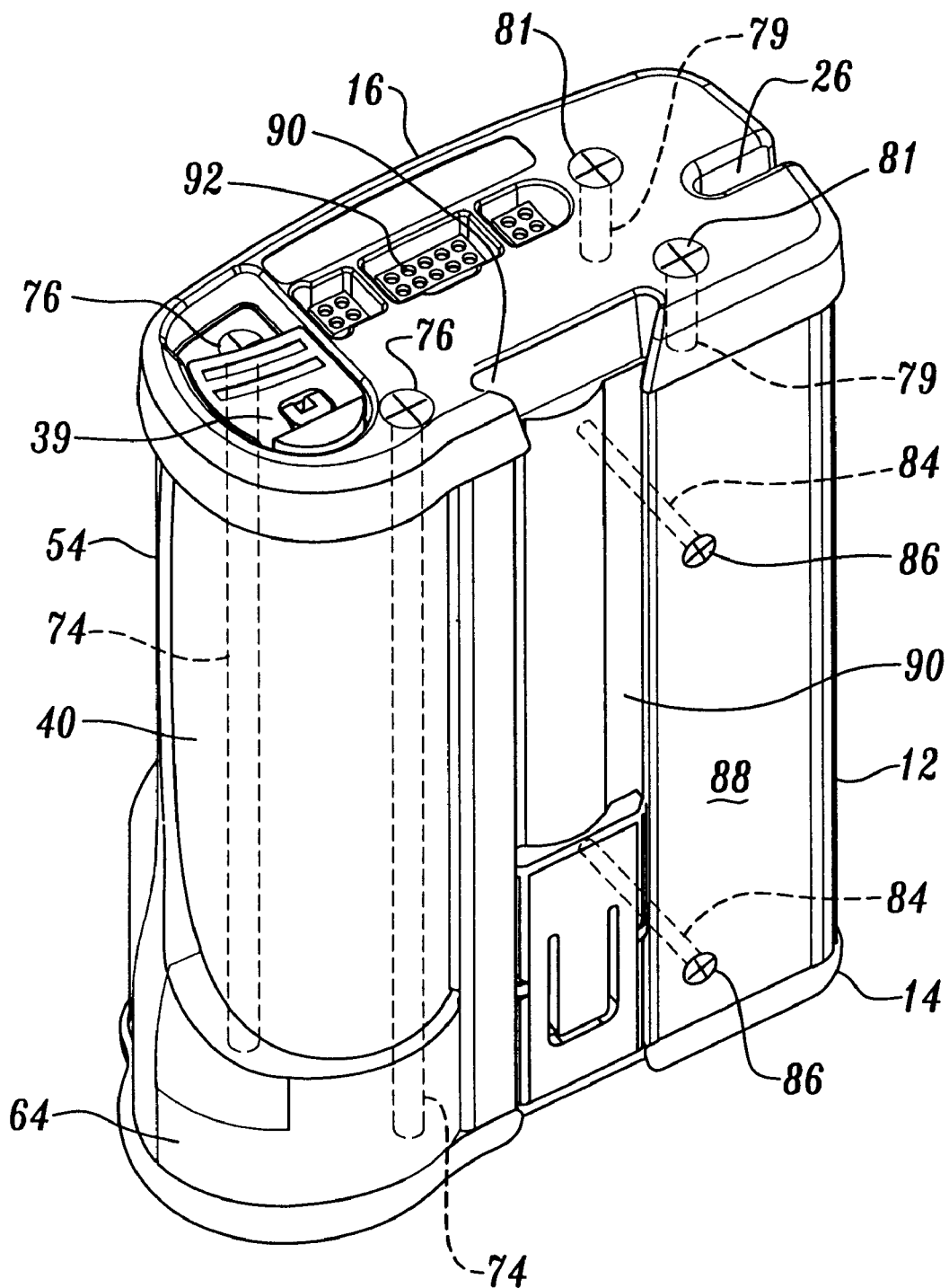

INFUSION PUMP EXTRUDED METAL HOUSING WITH ELASTOMERIC END CAPS

FIELD OF THE INVENTION

The present invention generally relates to a housing for a portable medical device, and more specifically, to a sealed metal housing for an ambulatory infusion pump, having shock absorbing ends.

BACKGROUND OF THE INVENTION

Housings for portable electronic devices are often fabricated from injection molded plastic to minimize production costs and weight. For example, in a typical plastic clam shell housing for such a device, the two halves of the plastic housing are connected together with fasteners; internal components are typically connected to one half of the housing using fasteners. However, in addition to being relatively lightweight, portable medical devices, such as ambulatory infusion pumps, must also be relatively rugged and resistant to mechanical shock and breakage if accidentally mishandled or dropped. Failure of a portable medical device due to undetected damage sustained in a short drop or as a result of other mechanical shock could be life threatening to a patient. Because infusions pumps of this type are often carried about by a patient for extended periods of time, they are likely to be frequently bumped and occasionally dropped. Lightweight plastic cases or conventional metal housings are generally unable to withstand such rough handling without damage to either the housing or the internal components of an ambulatory infusion pump. A further drawback to using plastic housings for such devices is that it is often necessary to include a metal plate or foil layer within the plastic material to shield against electromagnetic or radio frequency noise. The additional metal shielding adds weight and cost.

Also, because an ambulatory infusion pump may have to be coupled to a patient's vascular system at all times, even when the patient is bathing or showering, the infusion pump must be sufficiently watertight to be briefly immersed in water or exposed to water droplets in a shower. Providing a sealed, watertight housing for an infusion pump that has patient actuated controls and a display panel, and which accepts disposable pumping cassettes is not a trivial task, particularly when the housing must also be lightweight, rugged, and relatively low in cost, as noted above. Previous attempts to provide such a housing fabricated using injection molded plastic or metal have generally not been successful. It is somewhat difficult to provide sealed closure of a battery compartment and of the components that interact with a disposable cassette in a housing that is also lightweight, low cost, and capable of withstanding physical shock. Accordingly, it will be apparent that there is a need for such a housing that is not met by the available prior art.

SUMMARY OF THE INVENTION

In accord with the present invention, a housing for an ambulatory infusion pump is defined that is impact resistant, sealed and substantially watertight. The housing includes an extruded metal housing in which are disposed a battery compartment, an electronic component compartment, and a pump chassis. The extruded metal housing has opposed first and second ends in which corresponding first and second openings are respectively formed. A first overmolded cap that is sized to fit the first opening includes a substantially rigid internal member covered with an elastomeric material. Similarly, a second overmolded cap, which is sized to fit the second opening, also includes a substantially rigid internal member covered with the elastomeric material. A plurality of fasteners are provided for coupling the first and the second overmolded caps to the extruded metal housing so that the overmolded caps seal the first and the second openings.

The extruded metal body includes ports adapted for sealingly mounting a keypad and a display. An adhesive sheet seals around the ports and secures a bezel over the ports In addition, one of the first and the second caps preferably includes an opening into the battery compartment. A battery compartment cover seats within the opening and seals it.

Also included is a gripping surface that is applied to an exterior of the extruded metal body, to facilitate gripping the housing.

Either the first or the second caps includes an aperture through which a pump cassette ejection button extends for access from outside the housing. The aperture through which the pump cassette ejection button extends is sealed.

A preferred form of the invention includes means for mounting an accessory to the housing. Specifically, a pair of generally parallel grooves are formed on the surface of the extruded metal body for mounting a clamp or other accessory thereto.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1B is an isometric view of the rear surface and bottom of the housing for the pump;

DESCRIPTION OF THE PREFERRED EMBODIMENT

Figure 1A:
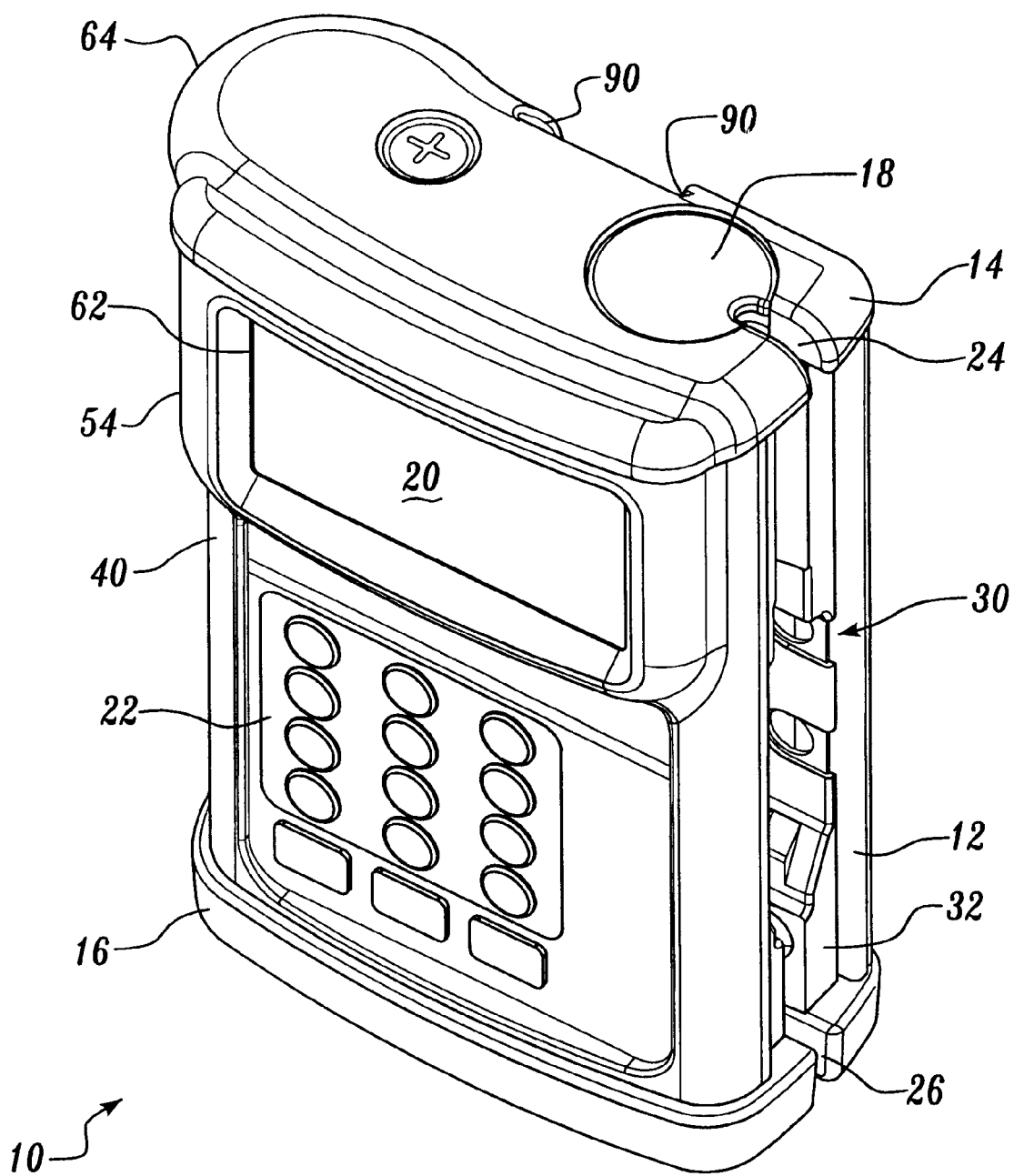
FIG. 1A is an isometric view showing the front, side, and top of an ambulatory infusion pump having a housing in accord with the present invention.

FIG. 1A illustrates an ambulatory infusion pump 10 having a housing in accord with the present invention. The housing includes an extruded case 12 that is preferably produced by extruding aluminum through an appropriately shaped die. The extruded case wraps around one side of the housing, sealing it on that side; however, an open side 30 is provided on the opposite side of the extruded case, for receiving a pump chassis 32 in which a pump cassette (not shown) is latched into a predefined position so that medicinal fluid can be infused into a patient. The housing includes a top cap 14 and a bottom cap 16. Both the top cap and bottom cap are formed of a rigid internal member having generally the same overall shape as its respective cap, but being slightly smaller in size. This internal rigid member is overmolded with synthetic rubber or another type of elastomeric material suitable for overmolding.

Use of the elastomeric material for top cap 14 and bottom cap 16 provides several advantages. First, it facilitates sealing the ends of extruded case 12 so that water or other liquid is excluded from the interior of the case where it might cause damage to the electronic circuitry contained therein. Secondly, the elastomeric material of the top and bottom cap provides mechanical shock absorbency in the event that the housing is dropped by a user or sustains a bump against a surface, since the elastomeric material has substantial resilience for absorbing shock upon impact. The internal rigid members used in the top and bottom cap are preferably fabricated from plastic, however, it is also possible to make the internal member from lightweight metal, such as aluminum. This internal member provides shape and strength to the top cap and bottom cap, without significantly reducing the resilient shock absorbency benefits of the elastomeric material with which the top and bottom cap are overmolded.

Figure 2:
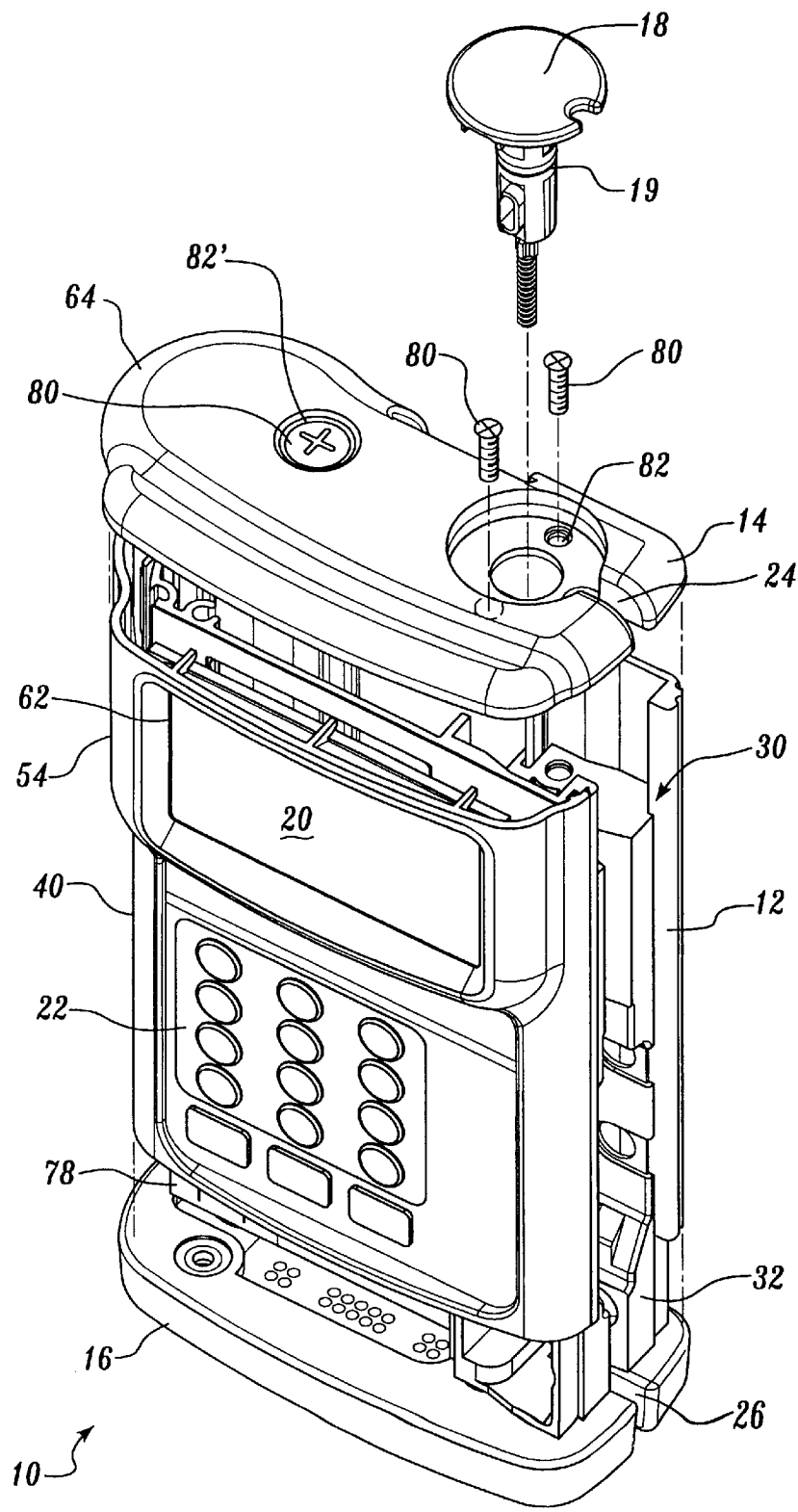
FIG. 2 is a partially exploded isometric view of the pump, showing the end caps spaced apart from an extruded metal case comprising the housing.
Figure 3:
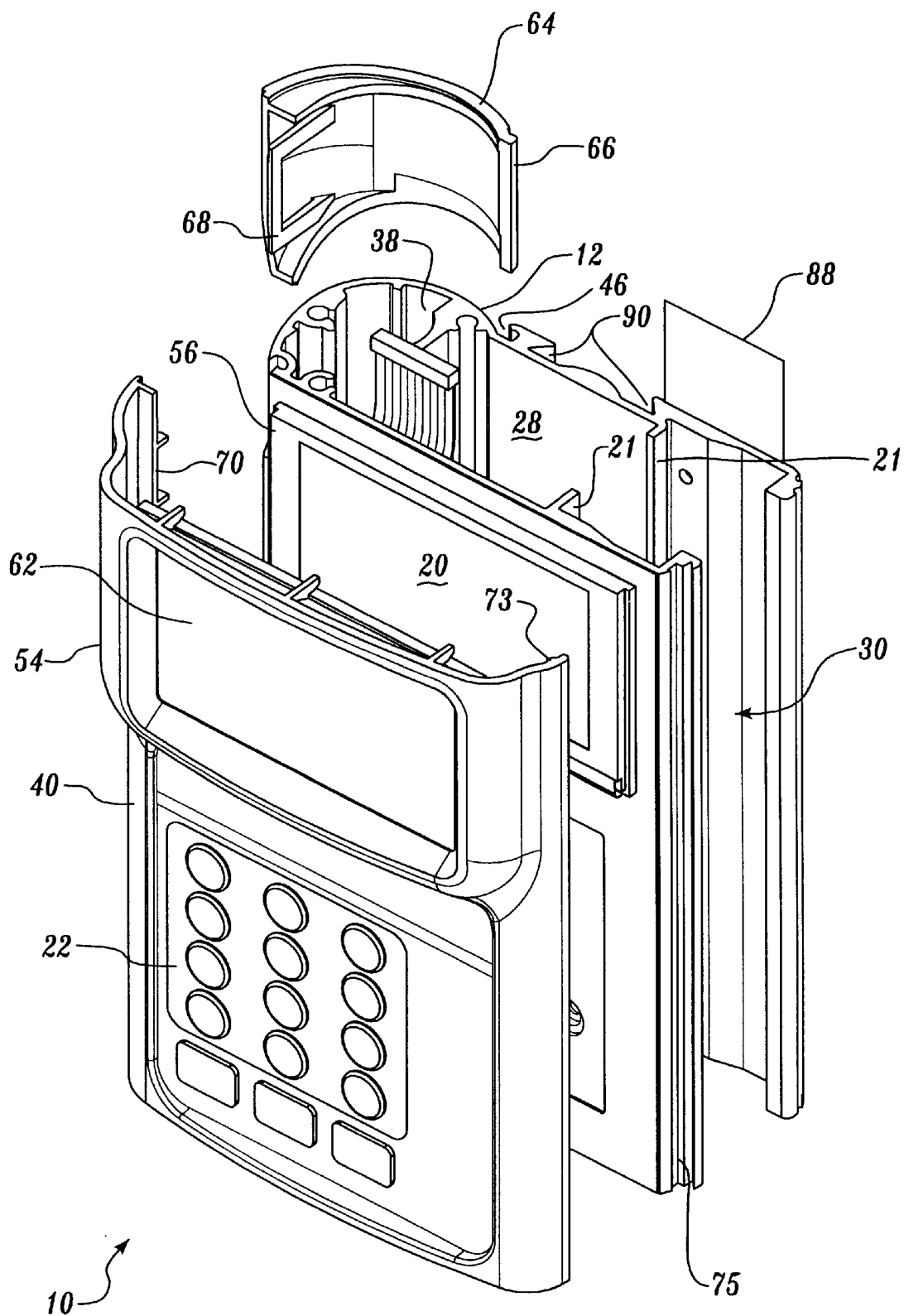
FIG. 3 is an exploded isometric view showing a bezel assembly, a display, and the extruded metal case.

As shown in FIG. 2, a pump cassette eject button 18 is inserted through top cap 14 and is sealed relative to an inner surface of the opening in the top cap with an O-ring 19. The pump eject button is depressed by a user to cause the pump cassette to be disengaged from pump chassis 32. Pump chassis 32 slides into open side 30 of extruded case 12 during assembly of the housing. Although not specifically indicated in the figures, strips of a silicone sealing material are provided along surfaces 21 (shown in FIG. 3) to seal against corresponding surfaces of pump chassis 32 so that the pump chassis effectively seals open side 30 of extruded case 12. Top cap 14 includes a notch 24 on its end overlying open side 30 of the extruded case, and bottom cap 16 includes a notch 26 that is generally aligned with notch 24. These two notches are shaped and sized to respectively receive a proximal tubing and a distal tubing (neither shown) that are coupled to the pump cassette when the pump cassette is latched into the predefined position within pump chassis 32.

Figure 4:
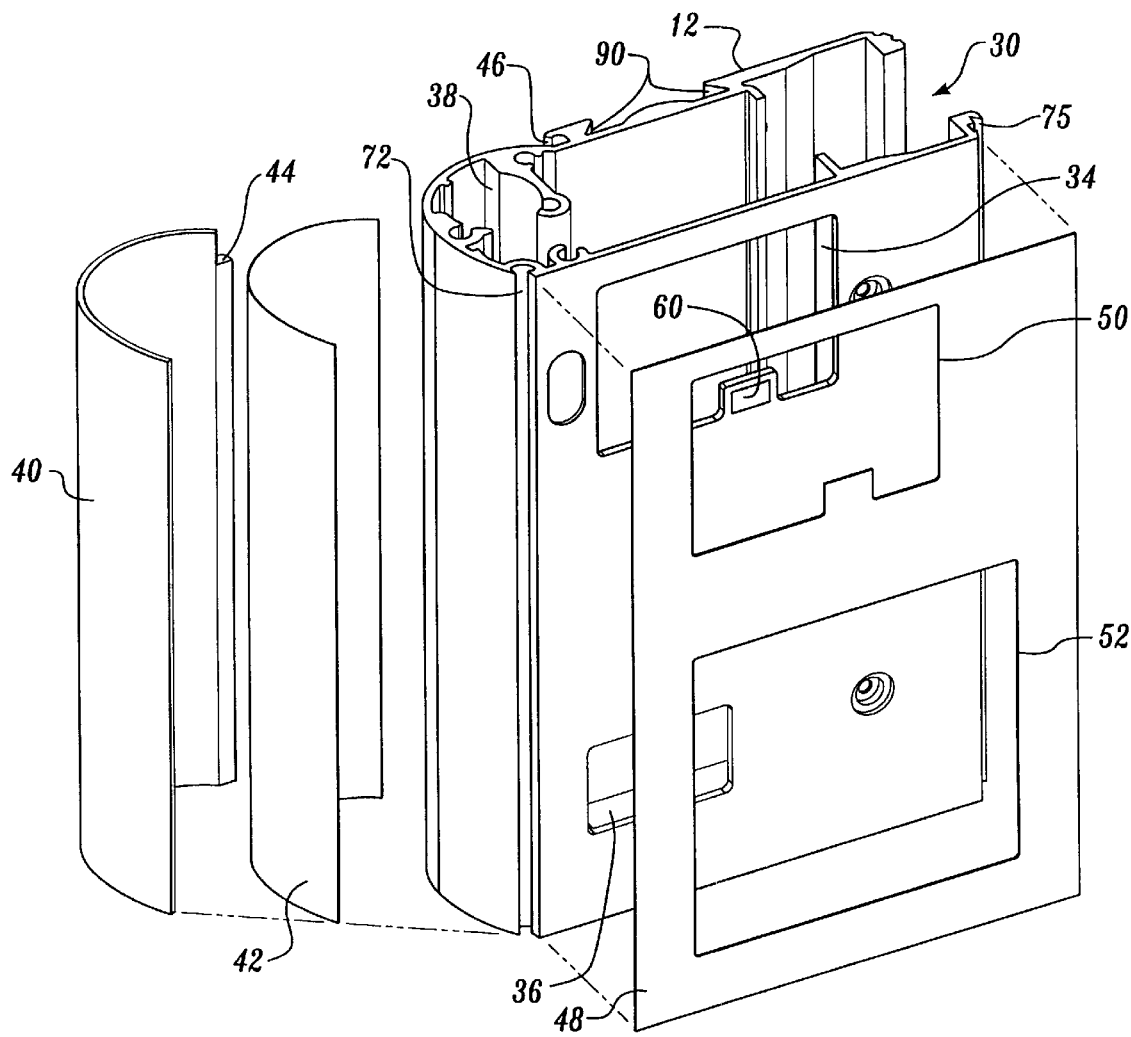
FIG. 4 is an exploded front view of the extruded metal case, a bezel adhesive sheet, a grip, and a grip adhesive sheet.
Figure 5:
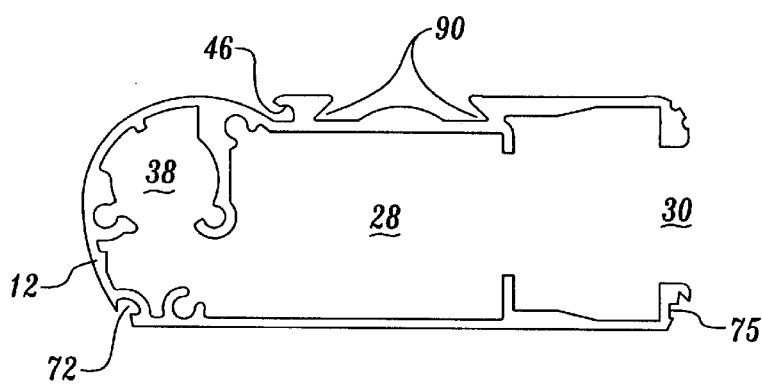
FIG. 5 is a top end view of the extruded metal case.

Referring to FIG. 4, it will be apparent that extruded case 12 includes a generally rectangular display port 34 near the top of its front surface and a generally rectangular keypad cable port 36 near the left corner of its front surface. A battery compartment 38 is disposed just inside the closed side of the extruded case and is sized to accept two storage batteries (not shown), which are inserted therein, coupled in series, with the positive terminal of one battery in contact with the negative terminal of the other. A removable battery compartment cover 39 (shown in FIG. 1B) is disposed in bottom cap 16 for providing access to battery compartment 38 for servicing the batteries, and otherwise seals the opening into the battery compartment.

Referring again to FIG. 4, a grip 40 extends around the closed side of extruded case 12 and is held in place by a grip adhesive sheet 42, which comprises a double-sided adhesive sheet, i.e., a sheet that is sticky on both its front and rear surfaces. The grip adhesive sheet adheres to the outer surface on the closed side of extruded case 12 and provides adhesion to hold grip 40 in place. In addition, grip 40 includes a flange 44 extending longitudinally along one of its edges, and this flange engages a groove 46 formed on the rear surface of the extruded case; groove 46 extends generally longitudinally along the length of the rear surface of extruded case 12. The end of groove 46 is clearly illustrated in FIG. 1B.

A bezel adhesive sheet 48, which also has double-sided adhesive surface, includes a display cutout 50 and a keypad cutout 52. The bezel adhesive sheet is used to adhesively secure a bezel assembly 54 to the front surface of extruded case 12. Before bezel assembly 54 is attached to the extruded case with bezel adhesive sheet 48, a display panel 56 (see FIGURES) is inserted into display port 34 and is held in place with display adhesive pads (not shown, which are double-sided adhesive disposed at the upper left and right corners on the rear surface of display panel 56. In addition, a tab 60 on extruded case 12 has a display adhesive pad (not shown) that uses double-sided adhesive to adhere to display panel 56, also holding the display panel in place in display port 34.

A clear plastic window 62 (FIG. 3) is provided in bezel assembly 54 overlying display panel 56. When bezel assembly 54 is adhesively attached to the front surface of extruded case 12, the bezel adhesive sheet effectively seals the undersurface of bezel assembly 54 around the periphery of the display assembly and keypad, preventing water or other liquid from entering the interior of the extruded case through display port 34 or keypad cable port 36. A cable (not shown) extends from a keypad 22 that is part of the bezel assembly and into the interior of extruded case 12 through keypad cable port 36, at the back surface of bezel assembly 54. This cable is attached to the circuitry within extruded case 12 to receive signals from keypad 22 when the keypad is actuated by the user.

A bezel tail 64 is disposed over the upper portion on the closed side of extruded case 12. A flange 66 on the rear edge of bezel tail 64 snaps into groove 46 on extruded case 12. A tab 68 formed on the other edge of bezel tail 64 engages bezel assembly 54 to hold bezel tail 64 in place.

On the inner surface of bezel assembly 54, a tab 70 is provided to engage the edge of a groove 72 formed on the adjacent surface of extruded case 12. Similarly, a tab 73 on the other side of bezel assembly 54 snaps into engagement with the edge of a groove 75 formed adjacent opening 30 on extruded case 12. The snap engagement of bezel assembly 54 with extruded case 12 further assures that bezel assembly 54 is adhesively attached to the extruded case in an appropriate position and provides additional holding force to secure the bezel assembly and bezel tail assembly in place.

A pair of long fasteners 74 extend the length of extruded case 12, passing through countersunk orifices 76 formed in bottom cap 16. Long fasteners 74 include threads that threaded into appropriately threaded inserts (not shown) within top cap 14, securing the top cap to bottom cap 16. Fasteners 79 pass through countersunk orifices 81 in bottom cap 16 and are threaded into inserts within pump chassis 32. It should be noted that a printed circuit board assembly 78 is connected into an appropriate edge connector (not shown) attached to the inner side of bottom cap 16. This printed circuit board assembly is slid into an electronic component compartment 28 within the interior of extruded case 12 as bottom cap 16 is secured to top cap 14.

As shown in FIG. 2, a pair of fasteners 80 extend through countersunk orifices 82 formed in top cap 14, under pump cassette eject button 18. The top cap fasteners are threaded into mating inserts disposed within the end of pump chassis 32. Also, as shown in FIG. 1B, a pair of fasteners 84 are inserted through countersunk holes 86 formed in the rear of extruded case 12 and are also used to hold pump chassis 22 in place within the extruded case. One of fasteners 84 (at the top of rear surface of the housing) extends through pump cassette eject button 18 to secure it in place within the pump chassis. FIG. 1B also shows a data port 92, which enables data connectors to be electrically coupled to the printed circuit board within the housing for transfer of data and control instructions.

A rear label 88 (FIG. 3) is adhesively applied to the rear surface of extruded case 12, overlying the portion of the extruded case in which pump chassis 32 is disposed. Also provided on the rear surface of extruded case 12, as shown in FIG. 1B, are a pair of parallel attachment grooves 90, which extend generally longitudinally along the length of the rear surface of the extruded case. Grooves 90 enable various attachments to be affixed to the rear of extruded case 12. For example, one attachment, which is not shown, comprises a clamp used to support the housing on a pole (also not shown) adjacent to where a patient is receiving fluid infused by the pump. Various other types of attachments can also be coupled to extruded case 12 by coupling into attachment grooves 90.

From the foregoing description, it will be apparent that the ends of extruded case 12 are generally sealed by top cap 14 and bottom cap 16 and that the display port and keypad cable port in the front surface of the extruded case are sealed with bezel adhesive sheet 48 that secures bezel assembly 54 to the front face of the housing. Further, pump chassis 32 sealingly closes open side 30 of extruded case 12. In this manner, the housing is made resistant to damage by exposure to water or other liquids. Furthermore, the elastomeric overmolding applied to top cap 14 and bottom cap 16 provides mechanical shock absorbency, minimizing the effect of accidental mishandling, in the event that the housing is bumped or dropped on either of its ends.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

What is claimed:

1. A housing for a portable medical device that protects against both mechanical shock and liquid intrusion into an interior of the housing, comprising:
   (a) a body having opposed openings disposed respectively at a first end and a second end;
   (b) a first elastomeric cap shaped and sized to sealingly seat within the opening disposed at the first end of the body;
   (c) a second elastomeric cap shaped and sized to sealingly seat within the opening disposed at the second end of the body; and
   (d) a plurality of fasteners for coupling the first and second elastomeric caps in sealing contact with the openings of the body, said first and second elastomeric caps providing a mechanical shock resistance to the housing.

2. The housing of claim 1, wherein the first and the second elastomeric end caps each comprise a plate formed of one of a plastic and a metal that is overmolded with an elastomeric material.

3. The housing of claim 1, wherein at least one of the first and the second end caps include orifices through which the plurality of fasteners extend, said orifices each including a countersunk opening disposed on an outer surface of said at least one of the first and the second end caps, each countersunk opening being sufficiently deep and sufficiently large in diameter to accept a head of one of the plurality of fasteners.

4. The housing of claim 1, wherein the plurality of fasteners extend from one of the first and the second elastomeric caps and are threaded into mating threaded fittings that are disposed in another of the first and second elastomeric caps.

5. The housing of claim 1, wherein the body includes a channel extending along one edge, said channel being closed by a pump chassis that sealingly fits within the channel.

6. The housing of claim 5, wherein the body defines a battery compartment that is accessed through an opening formed in one of the first and the second elastomeric caps, said one of the first and the second elastomeric caps including a cover that sealingly engages the opening.

7. The housing of claim 1, wherein the extruded metal body includes a port disposed in a surface thereof.

8. The housing of claim 7, wherein a bezel adhesive sheet sealingly adheres a bezel assembly over the port, sealing around a periphery of the port.

9. The housing of claim 8, wherein the bezel assembly includes a display portion and a keypad portion.

10. The housing of claim 1, wherein an electronic circuit assembly is coupled to one of the first and the second elastomeric caps.

11. The housing of claim 1, further comprising a grip disposed on a portion of an outer surface of the body.

12. The housing of claim 1, further comprising a compartment defined by the body and adapted to enclose at least one electronic circuit board.

13. The housing of claim 1, wherein a pair of generally parallel grooves are disposed along an outer surface of the body, said parallel grooves being adapted to engage an accessory.

14. A housing for an ambulatory infusion pump that is impact resistant, sealed and substantially watertight, comprising:
   (a) an body housing in which are disposed a battery compartment, an electronic component compartment, and an opening that is sealed with a pump chassis, said extruded metal housing having opposed first and second ends and corresponding first and second openings respectively disposed at the first and the second ends;
   (b) a first overmolded cap sized to fit said first opening, including a substantially rigid internal member covered with an elastomeric material;
   (c) a second overmolded cap sized to fit said second opening, including a substantially rigid internal member covered with the elastomeric material; and
   (d) a plurality of fasteners for coupling the first and the second overmolded caps to the body housing so that the first and the second openings are sealed thereby.

15. The housing of claim 14, wherein the plurality of fasteners are threaded into the body.

16. The housing of claim 14, wherein the body includes ports adapted for sealingly mounting a keypad and a display.

17. The housing of claim 14, wherein one of the first and the second caps includes an opening into the battery compartment.

18. The housing of claim 17, further comprising a battery compartment cover that seats within the opening and seals it.

19. The housing of claim 14, further comprising a gripping surface applied to an exterior of the extruded metal body, to facilitate gripping the housing.

20. The housing of claim 14, wherein one of the first and the second caps includes an aperture through which a pump cassette ejection button extends from outside the housing, said aperture being sealed around the pump cassette ejection, button.

21. The housing of claim 14, further comprising means for mounting an accessory to the housing.

22. A housing for an ambulatory infusion pump that is impact resistant, sealed and substantially watertight, comprising:
  (a) an extruded housing in which are disposed electronic circuitry and a pump chassis, said extruded housing having opposed first and second ends and corresponding first and second openings respectively disposed at the first and the second ends;
  (b) a first overmolded cap sized to fit said first opening, including a substantially rigid internal member covered with an elastomeric material;
  (c) a second overmolded cap sized to fit said second opening, including a substantially rigid internal member covered with the elastomeric material; and
  (d) a port formed in a surface of the extruded housing and covered by a bezel, an adhesive sheet sealing around a periphery of the port and adhesively attaching the bezel to the surface of the extruded housing.

23. The housing of claim 22, wherein the port comprises a port for mounting a display.

24. The housing of claim 22, wherein the bezel includes a keypad.

25. The housing of claim 22, further comprising a grip that is adhesively attached to a surface of the extruded housing.

26. The housing of claim 22, further comprising fasteners for connecting the first and the second overmolded caps to the extruded housing.

27. The housing of claim 22, further comprising a groove formed in a surface of the extruded housing and adapted for mounting an accessory thereto.

* * * * *

UNITED STATES PATENT AND TRADEMARK OFFICE
CERTIFICATE OF CORRECTION

PATENT NO. : 6,305,908 B1  
DATED : October 23, 2001  
INVENTOR(S) : Robert A. Hermann et al.

It is certified that error appears in the above-identified patent and that said Letters Patent is hereby corrected as shown below:

<u>Column 6,</u>  
Lines 14-15, replace "extruded metal body" with -- body --  
Lines 61-62, replace "extruded metal body" with -- body --  
Lines 66-67, replace "ejection, button" with -- ejection button --

Signed and Sealed this

First Day of October, 2002

Attest:

Attesting Officer

JAMES E. ROGAN  
*Director of the United States Patent and Trademark Office*